United States Patent [19]

Muz

[11] Patent Number: 5,035,243
[45] Date of Patent: Jul. 30, 1991

[54] HOLDER SLEEVE FOR POSITIONING A DETECTING AND MEASURING SENSOR

[75] Inventor: Edwin Muz, Reutlingen, Fed. Rep. of Germany

[73] Assignee: Nicolay GmbH, Fed. Rep. of Germany

[21] Appl. No.: 328,271

[22] Filed: Mar. 24, 1989

[30] Foreign Application Priority Data

Mar. 26, 1988 [DE] Fed. Rep. of Germany ....... 3810411

[51] Int. Cl.$^5$ .......................... A61B 5/024; A61B 5/02
[52] U.S. Cl. ..................................... 128/633; 128/687
[58] Field of Search ................. 128/633, 634, 664–666, 128/690, 687

[56] References Cited

U.S. PATENT DOCUMENTS

| | | | |
|---|---|---|---|
| D. 250,275 | 11/1978 | Bond | 128/633 |
| 3,810,460 | 5/1974 | Van Nie | 128/666 |
| 4,450,843 | 5/1984 | Barney et al. | 128/690 |
| 4,685,464 | 8/1987 | Goldberger et al. | 128/633 |
| 4,825,872 | 5/1989 | Tam et al. | 128/633 |
| 4,825,879 | 5/1989 | Tam et al. | 128/633 |
| 4,830,014 | 5/1989 | Goodman et al. | 128/666 |
| 4,867,165 | 9/1989 | Noller et al. | 128/633 |

*Primary Examiner*—Kyle L. Howell
*Assistant Examiner*—John Hanley
*Attorney, Agent, or Firm*—Roylance, Abrams, Berdo & Goodman

[57] ABSTRACT

A holder sleeve locks a detecting and measuring sensor into position, especially a detecting and measuring sensor for oximetric measurements, on the surface of a protruding part of a human body. The sensor includes a light source and a receiver which is sensitive to its radiation. The sleeve is elastically expandable and completely surrounds the body protruding part. each of two diametrically opposite sections of the sleeve has a recess opening to the sleeve inside surface or is radiation-permeable to receive and hold the transmitter or the receiver. Both portions of the sleeve lying between these sections have pluralities of folds following one another around the sleeve periphery, with each fold forming a spring.

10 Claims, 3 Drawing Sheets

Fig. 3
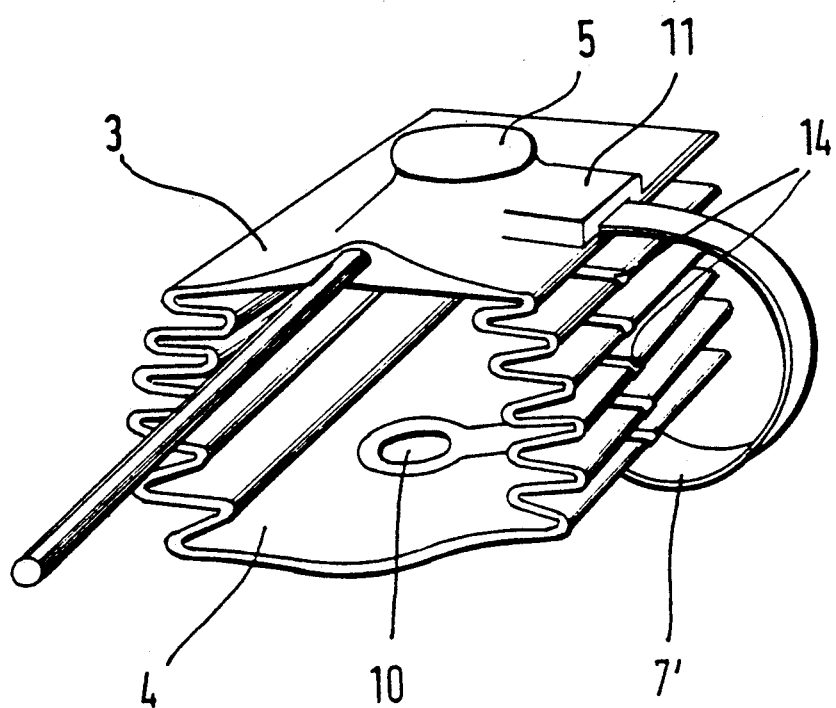
Fig. 6
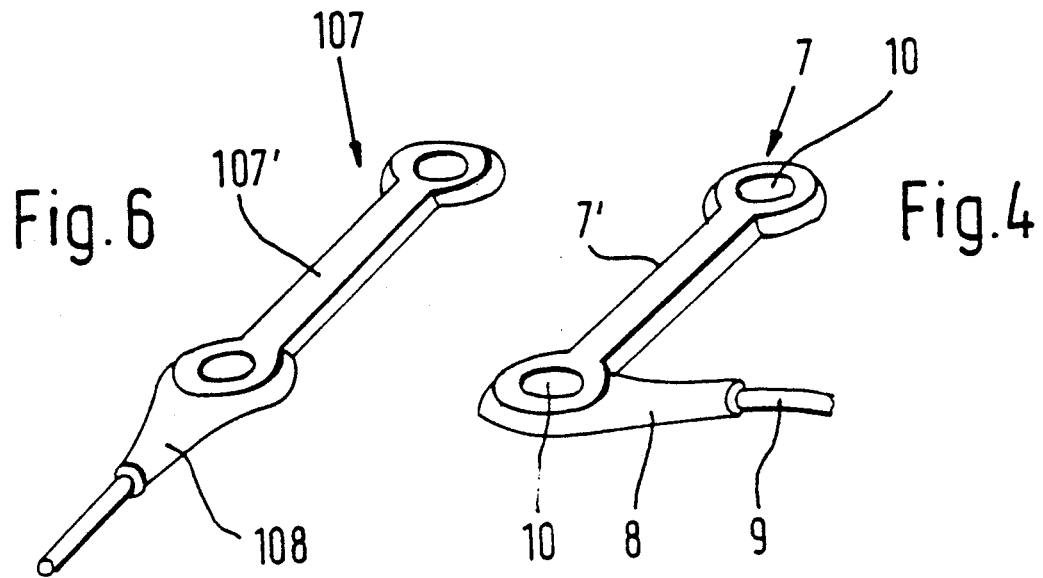
Fig. 4

HOLDER SLEEVE FOR POSITIONING A DETECTING AND MEASURING SENSOR

FIELD OF THE INVENTION

The present invention relates to a device for positioning a detecting and measuring sensor, especially a detecting and measuring sensor for oximetric measurements on the surface of a rod-like or protruding part of a human body. The sensor includes a light source transmitter and a receiver sensitive to the radiation emitted by the transmitter to be located on a diametrically opposite surface area portion of the body protruding part.

BACKGROUND OF THE INVENTION

A known device of this type, disclosed in U.S. Pat. No. 4,685,464, is intended for taking measurements on a finger, and is configured as a clothes line clip. An elastically flexible padding member is attached to each arm of the clip. The clip arms are loaded by means of a prebiased shank spring. The human finger is clamped between the two arms. A recess is provided in the surface of each padding member contacting the finger. The transmitter and the receiver lie in these recesses.

Such a device is costly, and has relatively large dimensions. Additionally, the device is not suitable for extensive engagement with the finger, since it can hinder movements of the finger being tested, and can also be slipped out of place or peeled off if such finger movements occur.

SUMMARY OF THE INVENTION

An object of the present invention is to provide a holder for a detecting and measuring sensor which can perform the measurements and obtain measurement results even over a long time period without having the mounting influence the results.

Another object of the present invention is to provide a holder for a detecting and measuring sensor which is simple and inexpensive to manufacture and of rugged construction.

The foregoing objects are obtained by a holder for securely positioning a sensor on a protruding part of a human body, which sensor includes a light source transmitter and a receiver sensitive to radiation emitted by the transmitter. The holder comprises an elastically expandable sleeve for completely surrounding the protruding part of the body. Two diametrically opposite sections on the sleeve have recesses for receiving the transmitter and the receiver and have means to permit radiation to pass between the body and the receiver and transmitter. Portions of the sleeve between the opposite sections have pluralities of folds adjacent one another around peripheral portions of the sleeve. The folds form springs and include inside angle parts defining at least a portion of a contact surface for engaging a body surface. The transmitter and the receiver are pressed against diametrically opposite surface areas of the body protruding part.

The sleeve according to the present invention holds the transmitter and the receiver securely in position on the surface of the part of the body to be tested, so that no fluctuation of the radiation can occur as a result of modification of the reflection on the surface and/or of the light path through the tissue. However, the pressure of the transmitter and receiver on the skin surface is so slight that the blood flow is not disturbed. Finally, the sleeve according to the present invention also facilitates the application of and then the removal of the light radiation transmitter and the receiver. Even relatively great differentials in the diameter of the part of the body on which the measurement is being carried out do not disturb the procedure. All of these features permit use of the device according to the present invention even when both the transmitter and receiver are placed on the arm or a leg of a small child or an infant, where the conditions especially require absolutely solid or stable resting points and very low pressure.

Preferably, the sleeve is configured as one unitary block member. Furthermore, it is advantageous to configure the recesses in the sleeve for holding the transmitter and receiver such that the recesses open only to the inside of the sleeve.

Such recesses guarantee a secure mounting on the skin surface in an especially simple manner. With recesses of this type and a sensor support member in the form of a strip having two ends on which the transmitter and the receiver are arranged, the part of the strip, lying between transmitter and receiver end parts of the support member, can then be arranged outside the sleeve member, if the sleeve is provided with a slot around a sleeve peripheral portion.

A channel can be formed in the sleeve which extends from one recess to a sleeve axial end and opens on the sleeve inside to receive a support member and/or the relevant connection cable. The support member and/or connection cable do not get in the way or have any other disturbing effect. The channel width can be diminished or reduced in the direction of the inside surface of the sleeve. This reduced width permits the support member and/or the connection cable to be introduced from the inside of the sleeve, while still providing a dependable fixing and immobilization of the device in the channel with simple means.

The folds can have angle sections having a more or less large elbow or bend radius. However, it is also possible to provide angle sections defining a concave inside curve and forming a relatively extensive contact surface between the sleeve and skin surface.

For measurements performed near the end of a member, for instance a finger, the folds on the device can be overlapping and across one axial end of the sleeve. The sleeve then has a shape similar to a bonnet or dome.

A double-walled configuration of the sleeve can be provided in the sections incorporating the transmitter and the receiver. An elastically flexible pressing contact of transmitter and receiver on the skin surface can be provided by the air cushion formed with the aid of the two walls. This is particularly advantageous when the holder for the transmitter and receiver is provided on the inside wall and is configured to be very thin and very flexible.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure:

FIG. 3 is a perspective view of the holder sleeve of FIG. 1;

FIG. 4 is a perspective view of a detecting and measuring sensor or device according to one embodiment of the present invention;

FIG. 6 is a perspective view of a detecting and measuring sensor or device according to another embodiment of the present invention;

DETAILED DESCRIPTION OF THE PREFERRED EMBODIMENTS

Figure 1:
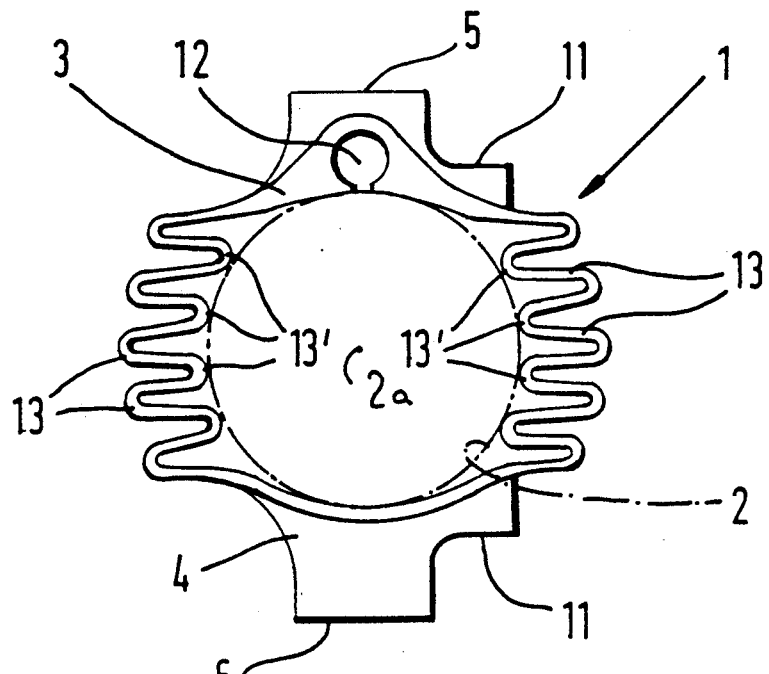
FIG. 1 is a front elevational view of a holder sleeve according to a first embodiment of the present invention.
Figure 2:
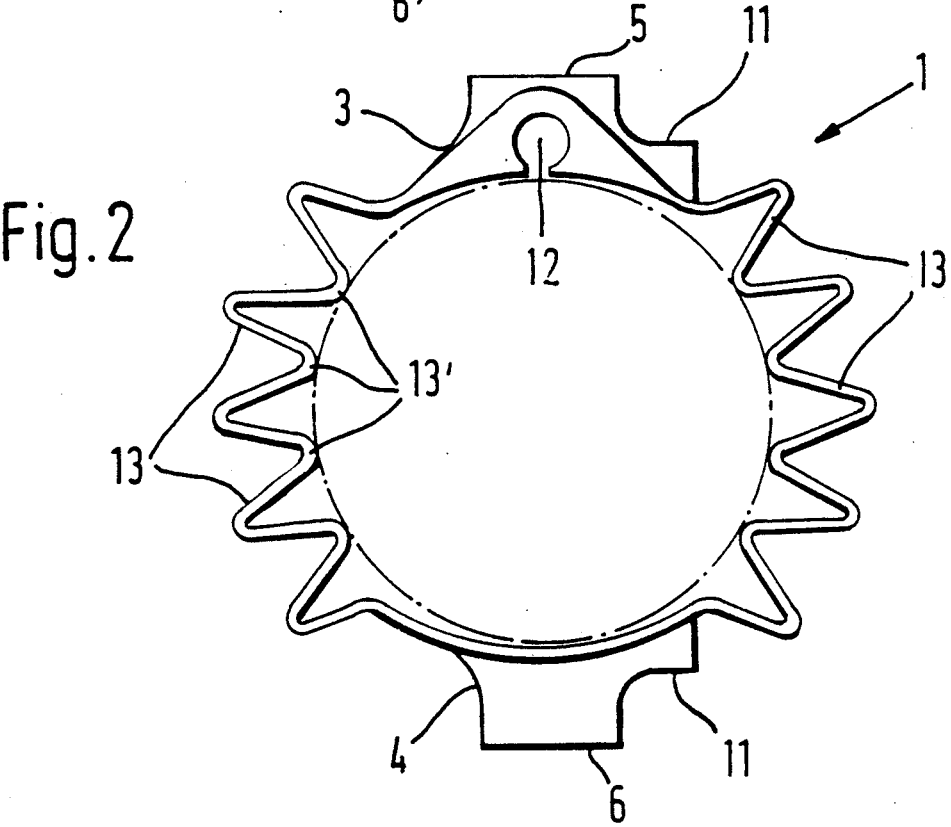
FIG. 2 is a front elevational view of the holder sleeve of FIG. 1 in an expanded state.

Referring initially to FIGS. 1-3, a sleeve according to the present invention is configured of one unitary piece, and produced of a flexible material such as rubber or silicon rubber. The sleeve locks an optical electronic detecting and measuring sensor (FIG. 4) into position for oximetric measurements on the skin surface of a human specimen for testing. Sensor 7 is disclosed in U.S. patent application Ser. No. 07/324,454, filed June 16, 1988 and entitled Sensor for Measuring Pulse Rate and/or Oxygen Saturation of Blood and Process for Making Same, the subject matter of which is hereby incorporated by reference.

As shown in FIG. 1, the sleeve, in the slackened state, has a contact surface formed by parts of the inner sleeve surface which defines a circular cylinder 2 shown with a dotted line and extending along a longitudinal axis 2a. Sections 3 and 4 of sleeve 1 are opposite each other. Each section extends over approximately one fourth of the periphery of the sleeve in its slackened state. In the middle of each section, a truncated conical or frustoconical recess is provided. The recesses open to the inside of the sleeve, and produce corresponding protuberances 5 and 6 on the outside of the sleeve. The shapes and sizes of the two recesses are adapted to the two truncated conical or fructoconical end sections of detecting and measuring sensor 7. The two sensor end sections have a transmitter and a receiver.

As shown in FIG. 4, the two ends of detecting and measuring sensor 7 are connected with each other by a flexible strip-like middle part 7'. A socket or brushing 8 is tip-stretched onto detecting and measuring sensor 7 for attaching connection cable 9 of detecting and measuring sensor 7.

The two end sections of detecting and measuring sensor 7 are forced head-on into the two recesses of sections 3 and 4, with the optical viewing window 10 opening inwardly The recesses hold the sensor end sections tightly in the manner of a push-button catch on account of the truncated conical shape. The strip-like middle part 7' can be guided on the outside of the sleeve between the two sections 3 and 4. A channel extending from each of the two recesses at right angles to the lengthwise or longitudinal axis of sleeve 1, opens to the inside of the sleeve. The middle part 7' is tightly held in the channel by being loosely clamped at its end parts only. Each of these two channels forms a corresponding angled projection 11 on the outsides of sections 3 and 4. A channel 12 extending parallel to the sleeve lengthwise axis opens in the recess of section 3, shown in FIGS. 1 to 3 at the top, to receive socket 8 and connection cable 9. This channel 12 opens laterally in the form of a narrow longitudinal slot to the inside of the sleeve. As a result of the elasticity of section 3, this slot can be expanded temporarily to the degree required for insertion of socket 8 and connection cable 9 into channel 12.

Both of the diametrically opposite portions of sleeve 1, connecting sections 3 and 4 with each other, comprise a plurality of folds 13 adjacent and following one another around the periphery of the sleeve. The inside or inner angle parts 13' form parts of the contact surface. As shown in FIG. 1, in the slackened state, the folds 13 form two springs between the two sections 3 and 4. Each fold 13 has an approximately U-shaped cross section.

The diameter of circular cylinder 2 is selected so that sleeve 1 is subjected to only a certain degree of expansion when it is thrust on the body part on which the measurement is to be carried out. The springs formed by folds 13 are biased or stressed sufficiently to position and retain the transmitter and the receiver of detecting and measuring sensor 7 securely on the skin surface, without exerting an undue contact pressure either in the area of the detecting and measuring sensor or in the area of the contact surface of sleeve 1. Even when sleeve 1 must be expanded relatively greatly, as is shown in FIG. 2, the pressure the sleeve exerts on the skin surface is increased only slightly, because the springs formed by folds 13 have a very supple characteristic angle dimension. With a greater expansion of folds 13, the folds adopt a V-shaped cross-sectional profile. By virtue of the high elasticity of sections 3 and 4 of sleeve 1, as well as the extensive adaptation capacity of folds 13, a good contact of sleeve 1 on the skin surface is guaranteed, even when the expanded sleeve 1, as is often the case, deviates markedly from the shape of a cylinder.

In order to be able to introduce detecting and measuring sensor 7 into sleeve 1 or to remove it therefrom, and to be able to guide or locate middle part 7' outside sleeve 1 extending from section 3 to section 4, a slot 14 is formed in one of the sleeve lateral portions connecting sections 3 and 4. Slot 14 extends from the channel provided in section 3, through folds 13 to the corresponding channel in section 4. In order to guide middle part 7' through slot 14, the slot can be widened as much as necessary due to the flexibility and resiliency of the sleeve.

Figure 5:
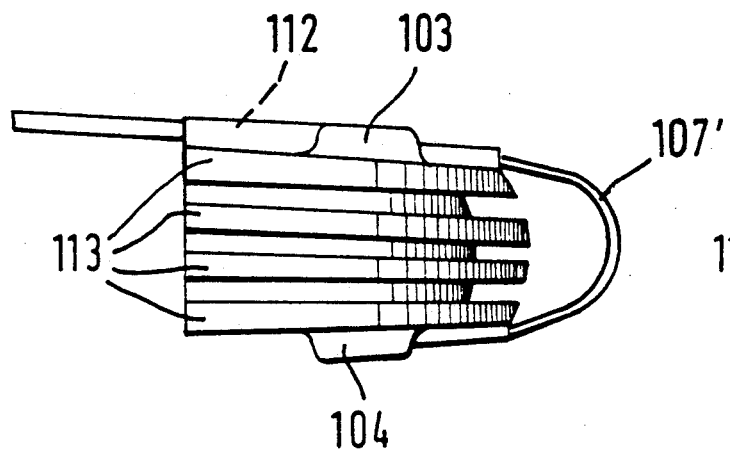
FIG. 5 is a side elevational view of a holder sleeve according to a second embodiment of the present invention.
Figure 7:
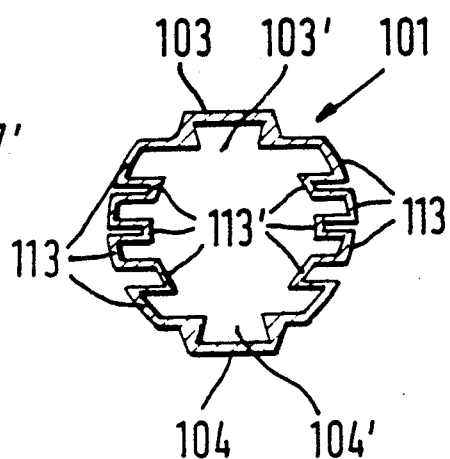
FIG. 7 is a side elevational view in section of the holder sleeve of FIG. 5.

The second embodiment, shown in FIGS. 5-7, is intended for measurements on a finger or toe. The sleeve 101 is formed of elastic material, for example, rubber or silicon rubber, and has two diametrically opposite sections 103 and 104. Each section has a recess 103' or 104', respectively, opening toward the inside of the sleeve. A channel opening to the sleeve inside extends from each of the two recesses 103' and 104' in the lengthwise direction of sleeve 101 to receive the strip-like middle part 107' of the relevant detecting and measuring sensor 107. A channel 112 extends in the opposite direction from recess 103' for receiving the socket 108 which is tip-stretched around detecting and measuring sensor 107, as shown in FIG. 6. In this second embodiment, socket 108 extends in the direction of middle part 107'.

Two groups of folds 113 adjacent and following one another around the sleeve periphery, as in the first embodiment, form two springs between sections 103 and 104 of sleeve 101. Deviating from the shape of folds 13 of the first embodiment, the profile of folds 113 follows a more meandering path. The innermost angle parts 113' form concavely curved longitudinal zones of a cylindrical surface. The contact surface of sleeve 101, in its slackened state, is the same as in the first embodiment, i.e., has a cylindrical shape. In the area of folds 113, the contact surface of sleeve 101 is considerably larger than when the folds have a U-shaped or V-shaped profile. The outside angle parts of folds 113 have elbows which appear to be concave when viewed from the inside of sleeve 10 outward. With expansion of sleeve 101, the protruding parts of folds 113 are deformed immediately. The protruding parts connect the angle parts with each other. FIG. 7 also clearly shows the truncated conical cross-sectional shape of recesses 103' and 104'. The recesses of the first embodiment also have a corresponding shape.

As shown in FIG. 5, folds 113 extend out over the contact side of sleeve 101, on which middle part 107' of detecting and measuring sensor 107 is guided between section 103 and section 104. Over this contact side of sleeve 101, folds 113 extend outwardly along the arc of a circle from one side to the other side. Thus, folds 113 extend between the sleeve sides without interruptions in folds 113.

Figure 8:
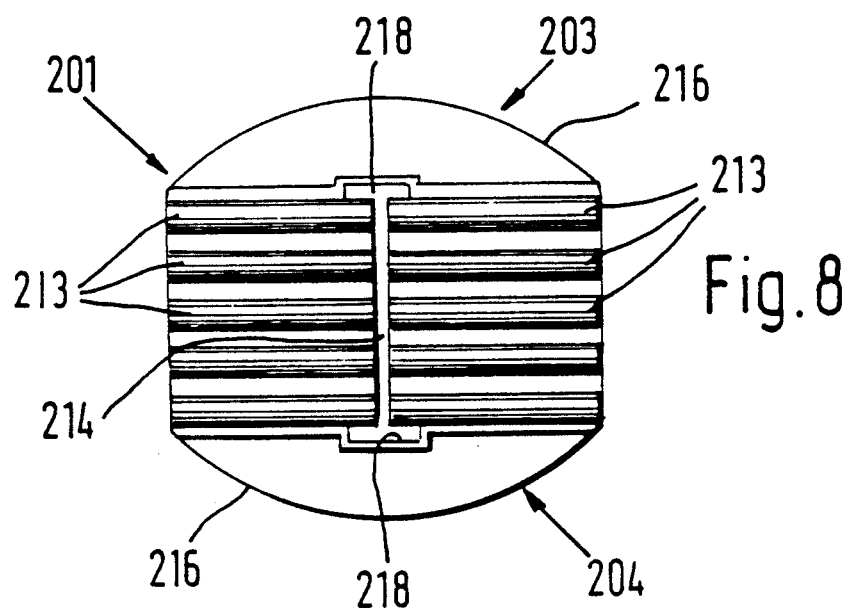
FIG. 8 is a side elevational view of a holder sleeve according to a third embodiment of the present invention.
Figure 9:
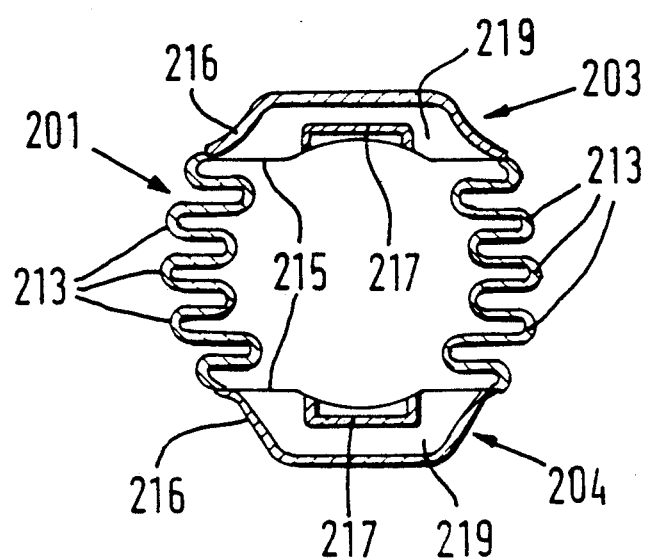
FIG. 9 is a side elevational view in section of the holder sleeve of FIG. 8.

The third embodiment, shown in FIGS. 8 and 9, includes folds 213 which are configured identically to folds 13 of the first embodiment. Folds 213 form springs between the two diametrically opposite sections 203 and 204 of the sleeve 201. Only these sections 203 and 204 differentiate sleeve 201 from the first embodiment. Sections 203 and 204 each comprise an inside wall 215 configured as one piece with folds 213, but thinner and more flexible than the folds, and comprise a considerably thicker but still flexible outside wall 216. These two jar-like outside walls 216 are gas-tight and are connected, in the third embodiment, by being melted along their edges, together with inside walls 215, and along the longitudinal sides in the areas where they pass over into folds 213. The spaces between inside walls 215 and outside walls 216 are filled with air.

A holder 217 is connected tightly with inside wall 215 both in section 203 and in section 204 arranged between inside wall 215 and outside wall 216. Each holder receives the transmitter or the receiver, respectively, and holds it tightly in the manner of a push-button or snap-type catch. The relevant detecting and measuring sensor is configured identically to detecting and measuring sensor 107, with channels for the socket and the middle part of the detecting and measuring sensor opening into the one holder 217 in section 203, and with a channel receiving the sensor middle part in the other holder in section 204. The channels 118 are illustrated in FIG. 8 for receiving the sensor middle part. A slot 214 extends from one channel 218 to the other channel 218 in the folds 213 of one sleeve side for arranging the middle part of the detecting and measuring sensor outside the sleeve.

FIG. 8 also shows the spherical indented shape of the two outside walls 216 which are formed by a subsequently applied covering. Walls 215 and 216 form two chambers 219 filled with air. Since the two sections 203 and 204 each form an air cushion supporting the transmitter or respectively the receiver, this third embodiment of the invention provides a special positioning of the transmitter and the receiver, capable of enhanced adapting to the body surface being measured because of the improved pliant spring characteristic of the transmitter and receiver mounting.

All of the embodiments of the holder sleeve according to the invention can be manufactured simply and at low cost, are simple to clean and are easy to apply. Furthermore, the dimensions can fall within a very wide range of different possible diameters, without modifying the contact pressure by a great amount.

While various embodiments have been chosen to illustrate the invention, it will be understood by those skilled in the art that various changes and modifications can be made therein without departing from the scope of the invention as defined in the appended claims.

What is claimed is:

1. A holder for securely positioning a sensor on a protruding part of a human body, which sensor includes a light source transmitter and a receiver sensitive to radiation emitted by the transmitter, comprising:
   an elastically expandable sleeve having an inside surface surrounding a longitudinal axis adapted to receive and surround a protruding part of a body;
   two diametrically opposite sections on said sleeve, each of said sections having recess means on said inside surface opening toward said axis for receiving one of the transmitter and the receiver and to permit radiation to pass through the body between the receiver or transmitter; and
   portions of said sleeve between said opposite sections having pluralities of folds adjacent one another around said sleeve in a circumferential direction of said sleeve, each of said folds including inner angle parts defining at least a portion of a contact surface for engaging a body surface, said folds forming a spring;
   whereby, a transmitter and a receiver received in said recess means can be pressed against diametrically opposite surface areas of a body protruding part.

2. A holder according to claim 1 wherein said sleeve is one, unitary piece.

3. A holder according to claim 1 wherein said recess means open only on said inside surface of said sleeve.

4. A holder according to claim 3 wherein said sleeve includes a slot extending from one of said recess means, around one of said portions and to the other of said recess means.

5. A holder according to claim 1 wherein said sleeve includes axial ends; and
   one of said opposite sections includes a channel extending longitudinally from the recess means therein to one of said axial ends of said sleeve and opening on said inside surface of said sleeve.

6. A holder according to claim 5 wherein said channel has a width of decreasing dimensions toward said inside surface.

7. A holder according to claim 1 wherein said folds define a winding contour in transverse cross section relative to said axis; and said angle parts define points on a inside peripheral curve, said curve being concave relative to said axis of said sleeve.

8. A holder according to claim 1 wherein said sleeve includes axial ends; and
   said folds extend over and across one axial end of said sleeve.

9. A holder according to claim 1 wherein
each of said opposite sections comprise inside and
outside walls forming an air cushion therebetween;
said inside walls are elastic membranes and have said
recess means which open inwardly toward said axis.

10. A holder according to claim 9 wherein
said outside walls are a covering over said inside walls.

* * * * *